United States Patent [19]

Ficken et al.

[11] Patent Number: 4,996,141

[45] Date of Patent: Feb. 26, 1991

[54] MONOMETHINE COMPOUNDS

[75] Inventors: Geoffrey E. Ficken, Wilmslow; Douglas J. Edwards, Warrington; Clive W. Mowforth, Wilmslow; Trevor J. Maternaghan, Knutsford, all of England; Rolf Steiger, Praroman, Switzerland; Victor W. Dolden, Wilmslow, England

[73] Assignee: Ilford Limited, Cheshire, England

[21] Appl. No.: 295,795

[22] Filed: Jan. 11, 1989

[30] Foreign Application Priority Data

Jan. 13, 1988 [GB] United Kingdom ................. 8800662

[51] Int. Cl.$^5$ ............................................... G03C 1/16
[52] U.S. Cl. .................................... 430/583; 430/567; 430/574; 548/181
[58] Field of Search ............... 430/583, 574, 595, 567; 548/181

[56] References Cited

U.S. PATENT DOCUMENTS

| 3,156,685 | 11/1964 | Nys et al. | 260/240.6 |
| 3,424,586 | 1/1969 | Gotze | 96/106 |
| 3,816,131 | 6/1974 | Kampfer et al. | 96/29 |
| 4,210,715 | 7/1980 | Fujiwhara et al. | 430/439 |
| 4,469,785 | 9/1984 | Tanaka et al. | 430/572 |
| 4,609,621 | 9/1986 | Sugimoto et al. | 430/567 |
| 4,769,316 | 9/1988 | Miyasaki et al. | 430/570 |

OTHER PUBLICATIONS

Gershtein et al., Chemical Abstracts, vol. 97, No. 12, Sep. 20, 1982, page 82, No. 93957h.

Primary Examiner—Paul R. Michl
Assistant Examiner—Mark R. Buscher
Attorney, Agent, or Firm—Wenderoth, Lind & Ponack

[57] ABSTRACT

Compounds of the formula

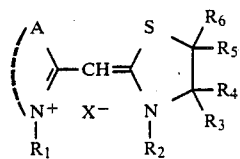

where A represents the atoms necessary to complete a benzoxazole or naphthoxazole ring which is optionally substituted, $R_1$ and $R_2$ are each alkyl, hydroxyalkyl or alkoxy alkyl groups wherein the alkyl moiety comprises 1 to 4 carbon atoms, $R_3$, $R_4$, $R_5$ and $R_6$ are each hydrogen atoms or alkyl groups having 1 to 4 carbon atoms or phenyl groups, and X is an anion.

10 Claims, No Drawings

MONOMETHINE COMPOUNDS

This invention relates to novel monomachine compounds, to their production and to their use in silver halide photographic materials.

Therefore according to a first aspect of the present invention there are provided monomethine compounds of the general formula I:

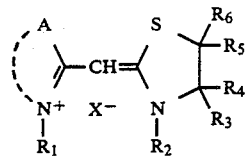

where A represents the atoms necessary to complete a benzoxazole or naphthoxazole ring which is optionally substituted, $R_1$ and $R_2$ are each alkyl, hydroxyalkyl or alkoxy alkyl groups wherein the alkyl moiety comprises 1 to 4 carbon atoms, $R_3$, $R_4$, $R_5$ and $R_6$ are each hydrogen atoms or alkyl groups having 1 to 4 carbon atoms or phenyl groups, and X is an anion.

Examples of optional substitution in A include halogen atoms or alkyl or alkoxy group shaving 1 to 4 carbon atoms or phenyl groups.

The preferred monomethine compounds of formula I are those wherein A represents the atoms necessary to complete a benzaxozole or naphthazole ring which is unsubstituted or substituted by alkyl or alkoxy each having 1 to 4 carbon atoms, halogen or phenyl, $R_1$ and $R_2$ are each alkyl or alkoxy alkyl wherein the alkyl moiety comprises 1 to 4 carbon atoms, $R_3$, $R_4$, $R_5$ and $R_6$ are each hydrogen, alkyl having 1 to 4 carbon atoms or phenyl and X is $ClO_4^-$, $BF_4^-$ or a halide.

Most preferably $R_1$ and $R_2$ are each methyl groups.

Particularly preferred monmethine compounds are compounds A to N as set forth in the Examples which follow.

The compounds of the formula I may be prepared by reacting a compound of formula II

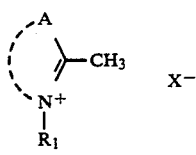

with a compound of formula III

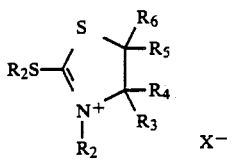

where A, $R_1$–$R_6$ and X have the meanings assigned to them above, at an elevated temperature in the presence of a basic condensing agent. The preferred temperature range is from 80° to 140° C.

Suitable condensing agents are pyridine and triethylamine for this reaction and those which follow.

Alternatively when $R_1$=$R_2$ compounds of formula I may be prepared by heating together compound IV

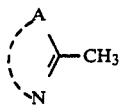

with compound V

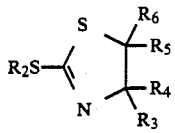

where $R_2$–$R_6$ have the meanings assigned to them above with an excess of a sulphonic ester of the formula $R_7$—$SO_3$—$R_2$ where $R_2$ has the meaning assigned to it above and $R_7$ is an alkyl or aryl group, followed by heating in the presence of a basic condensing agent.

Compounds of formula I may alternatively be prepared by reaction of compound VI:

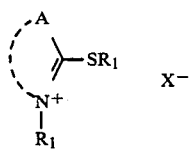

with a compound VII

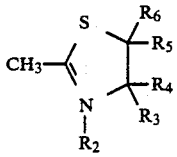

in the presence of a basic condensing agent wherein A, $R_1$–$R_6$ and X are as defined above.

When $R_1$=$R_2$, compounds of formula I may be prepared by heating together a compound of formula VIII

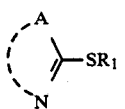

a compound of formula IX

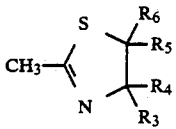

with an excess of a sulphonic ester $R_7SO_3R_2$, followed by heating, preferably to reflux, in the presence of a basic condensing agent.

The most suitable basic condensing agent is pyridine for this reaction.

Compounds of formula I absorb in the U-V part of the spectrum but exhibit a useful effect when added to a silver halide emulsion as they improve the overall white light speed of the emulsion. They also appear to improve the inherent sensitivity of the silver halide grains and decrease reciprocity failure at long exposure times.

The compounds of formula I are of particular use to improve the inherent sensitivity of silver halide emulsions wherein the silver halide crystals are of the tabular habit, that is to say wherein the aspect ratio of the crystals is greater than 5:1. This is demonstrated in some of the Examples which follow.

The compounds of formula I may also be used to boost the inherent blue light sensitivity of silver halide emulsions in cases where this is useful and one Example illustrates this. One other Example shows the effect when a compound of formula I is present in a silver halide emulsion which has been optically sensitised with a green sensitising dye. This Example shows that reciprocity failure is reduced at long exposure times.

When the compound of formula I is present in a silver halide emulsion it is present in the range from 50 mg per mole to Ag to 700 mg per mole of Ag.

When the compound of formula I is present in a silver halide emulsion which has tabular silver halide grains preferably it is present in the range of from 100 mg per mole of Ag to 400 mg per mole of Ag.

When the compound of formula I is present in a polydisperse silver halide emulsion having cubic grains preferably it is present in the range of from 350 mg per mole of Ag to 650 mg per mole of Ag.

The silver halide emulsion in which the compound of formula I is present may have been chemically sensitised by any of the well known means for example by use of sulphur, selenium and noble metals. Examples of suitable sensitising compounds are sodium thiophosphate and thiocyanate and mercury, gold, palladium and platinum salts.

The silver halide of the emulsion is preferably a predominantly bromide emulsion comprising at least 80% bromide by mole %. A particularly suitable emulsion comprises 94% by mole % bromide and 6% mole % of iodide.

The emulsion may contain any of the additives commonly used in photographic emulsions for example wetting agents, stabilising agents, polyethylene oxides, metal sequestering agents and growth or crystal habit modifying agents commonly used for silver halide such as adenine.

Preferably the dispersing medium is gelatin or a mixture of gelatin and a water-soluble latex for example a latex vinyl acrylate-containing polymer. Most preferably if such a latex is present in the final emulsion it is added after all crystal growth has occurred. However other water-soluble colloids for example casein, polyvinylpyrrolidone or polyvinyl alcohol may be used alone or together with gelatin.

The photographic base may be any of the bases used for photographical film materials for example transparent bases such as cellulose triacetate, cellulose acetate-butyrate or biaxially orientated polyethylene terphthalate or opaque bases such as baryta coated paper base of polyethylene coated paper base.

The following Examples will serve to illustrate the invention.

EXAMPLE 1

A.
3-Methyl-2-[(3-methyl-2-thiazolidinylidene)-methyl)]-benzoxazolium iodide

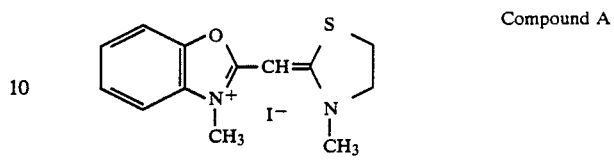

Compound A

A mixture of 2-methylbenzoxazole (13.3 g), 4,5-dihydro-2-(methylthio)-thiazole (20.0 g), and methyl p-toluene-sulphonate (55.9 g) was heated in an oil-bath at 140° C. for five hours. Pyridine (100 ml) was added, and the mixture was refluxed for 30 minutes. The solution was poured, with stirring into a solution of sodium iodide (72 g) in water (150 ml), and the mixture was cooled. The resulting solid was filtered off and washed thoroughly with water. After drying, it was warmed with toluene and refiltered, and finally recrystallised from methanol.

The produce was obtained as pale cream-coloured crystals, m.p. 311°–312° C. (decomp.).

B.
3-Methyl-2-[(3-methyl-2-thiazolidinylidene)-methyl)]-benzooxazolium perchlorate

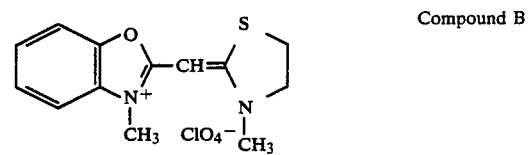

Compound B

Preparation as in A, but by treating the reaction mixture with aqueous sodium perchlorate solution, the product was obtained as pale cream-coloured crystals, m.p. 310°–312° (decomp) after crystallisation from pyridine.

EXAMPLE 2

3-Methyl-2-[(3-methyl-2-thiazolidinylidene)-methyl]-5-phenylbenzoxazolium iodide

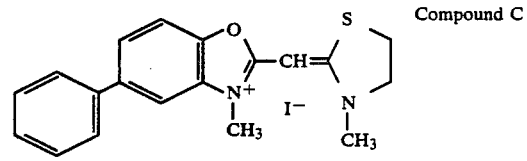

Compound C

A mixture of 2-(methylthio)-5-phenylbenzoxazole (14.5 g), 4,5-dihydro-2-methylthiazole (4.75 g), and methyl p-toluenesulphonate (28.0 g) was heated at 140° C. for four hours. Pyridine (50 ml) was added, and the mixture was refluxed for 40 minutes. The resulting solution was cooled and treated with water (100 ml), and the solid which separated was filtered off. The filtrate was treated with sodium iodide (30 g) and concentrated hydrochloric acid (50 ml). The precipitate was filtered off, washed with water, dried, warmed with toluene, and refiltered; it was finally crystallised from methanol to yield the product as pale yellow crystals, m.p. 264°-264° C.

By use of similar methods, the compounds of Examples 3-10 were prepared.

EXAMPLE 3

5-chloro-3-methyl-2-[(3-methyl-2-thiazolidinylidene)-methyl]-benzoxazolium bromide

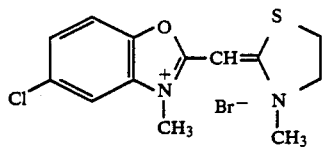

Compound D

The compound was obtained as pale yellow crystals, m.p. 318°-319° C. (decomp.), by crystallisation from methanol.

EXAMPLE 4

1-Methyl-2-[(3-methyl-2-thizolidinylidene)-methyl]-naphtho[1,2-d] oxazolium iodide

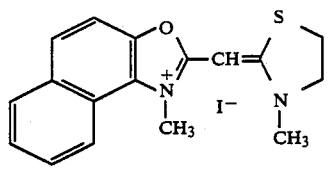

Compound E

The product was obtained as pale yellow crystals, m.p. 264°-265° C. (decomp.), by crystallisation from methanol.

EXAMPLE 5

2,5,6-Trimethyl-2-[(3-methyl-2-thiazolidinylidene)-methyl]-benzoxazolium bromide

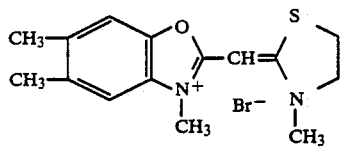

Compound F

After crystallisation from ethanol, the product was obtained as cream-coloured crystals, m.p. 306°-307° C. (decomp.)

EXAMPLE 6

5-Methoxy-3-methyl-2-[(3-methyl-2-thiazolidinylidene)-methyl)]-banzoxazolium iodide

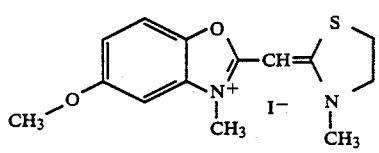

Compound G

The compound was obtained as cream-coloured crystals, m.p. 284°-285° C., by crystallisation from methanol.

EXAMPLE 7

2-[(3,5-Dimethyl-2-thiazolidinylidene)-methyl]-3-methylbenzoxiazolium iodide

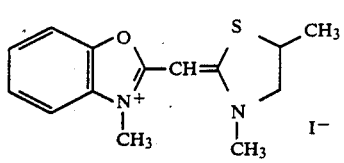

Compound H

The compound was obtained as cream-coloured crystals, m.p. 278°-279° C., by crystallisation from methanol.

EXAMPLE 8

3ethyl-2-[(3-ethyl-2-thiazolidinylidene)-methyl]-benzoxazolium iodide

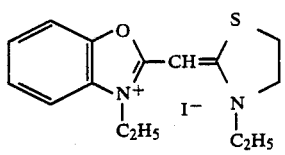

Compound I

The compound was crystallised from methanol, to give cream-coloured crystals, m.p. 248-250° C.

EXAMPLE 9

3-Methyl-2-[(3-methyl-5-phenyl-2-thiazolidinylidene)-methyl]-benzoxazolium iodide

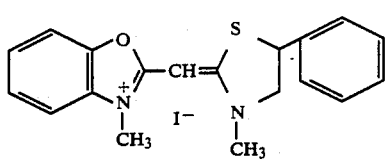

Compound J

After crystallisation from methanol, the product was obtained as pale yellow crystals, m.p. 260-261° C.

EXAMPLE 10

3-Methyl-2-[(3,4,4-trimethyl-2-thiazolidinylidene)-methyl]-benzoxazolium iodide

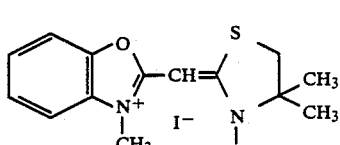

Compound K

After crystallisation from ethanol, the product was obtained as cream-coloured crystals, m.p. 257°-258° C. (decomp.).

EXAMPLE 11

3-(2-Methoxyethyl)-2-[(3-methyl-2-thiazolidinylidene)-methyl)]-benzoxazolium iodide

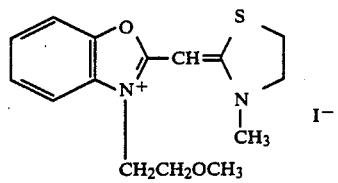

Compound L

Quaternary salts were prepared as follows:
(i) 2-Methylbenzoxazole (6.65 g) and 2-methoxyethyl p-toluenesulphonate (12.65 g) were heated together at 140° C. for 2 hours.
(ii) 4,5-Dihydro-2-(methylthio)-thiazole (8.0 g) and methyl p-toluenesulphonate (12.3 g) were heated together at 100° C. for 1.5 hours.

The products were combined, and refluxed for 40 minutes with pyridine (50 ml). The resulting solution was poured into a solution of sodium iodide (15 g) in water (150 ml), and concentrated hydrochloric acid (50 ml) was stirred in. The solid, which slowly crystallised out, was filtered off, was washed well with water, then ether, and dried. After crystallisation from ethanol, the compound was obtained as pale yellow crystals, m.p. 223°–225° C.

EXAMPLE 12

2-[(3-(2-methoxyethyl)-2-thiazolidene)-methyl]-3-methylbenzoxazolium tetrafluoro-borate

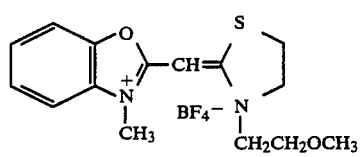

Compound M

The compound was prepared by a method similar to that of Example 11; after crystallisation from ethanol, it was obtained as pale yellow crystals, m.p. 142°–144° C.

EXAMPLE 13

2,5,7-Trimethyl-2-[(3-methyl-2-thiazolidin-ylidene)-methyl]-benzoxazolium bromide

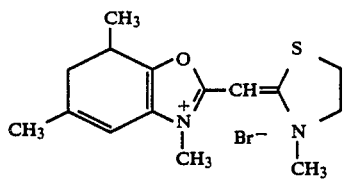

Compound N

By use of a method similar to that of Example 1, the compound was obtained as colourless crystals, m.p. 326°–327°, after crystallisation from methanol.

The compounds in the following use Examples are indicated in the preparation Examples. For Example compound B was prepared in Example 1.

Use with silver halide emulsions containing tabular silver halide crystals.

EXAMPLE 14

A silver halide emulsion was prepared which comprised silver halide crystals having an aspect ratio of 25:1 and a mean grain size of 0.62 μm (diameter of sphere of equivalent volume). The core of the crystals were pure bromide but 6 mol % iodide was distributed evenly in the remainder of the crystals. Gelatin was the binder.

Three series of tests using this emulsion were then carried out.

TEST 1

EMULSION NOT CHEMICALLY SENSITISED

Compound B 267 mg per mole of silver in methanol was added to the emulsion at 40° C. After 30 minutes the emulsion was coated on subbed polyester base to give a silver coating weight of 50 mg $dm^2$ and a gelatin coating weight of 97 mg $dm^2$. After the coating had dried it was cut into strips.

The strips were light exposed to 250 lux for a range of exposure times and developed in a developer I of the formula:

| Metol | 2 g |
|---|---|
| Hydroquinone | 5 g |
| Sodium sulphite | 100 g |
| Borax | 3 g |
| Sodium tripolyphosphate | 3.5 g |
| water to | 1 litre |
| for eight minutes at 20° C. | |

The results are shown in table 1. The foot speed (0.1 density units above fog, $S_{0.1}$) being shown for a range of exposure times.

TABLE 1

| | Exposure time in seconds | | |
|---|---|---|---|
| Coating | $t = 10^{-3}$ s | $t = 1$ s | $t = 60$ s |
| With Compound B ($S_{0.1}$) | 3.39 | 3.27 | 2.97 |
| Without Compound B ($S_{0.1}$) | 3.12 | 3.06 | 1.99 |

This shows that Compound B decreases low intensity reciprocity failure. The speed decrease at long exposure times is decreased by the presence of Compound B.

TEST 2

Emulsion Chemically Sensitised

Samples of the above tabular emulsion were optimally chemically sensitised by being digested at 52° C. with sulphur and gold in the presence of sodium thiocyanate. The emulsion was then stabilised by addition of a solution of 4-hydroxy-b-methyl-1,3,3a,7-tetraazaindene stailiser. After 30 minutes various amounts of Compounds B, C and E, were then added as methanolic solutions to individual portions of the above emulsion.

All the emulsions were then coated on subbed polyester at a silver coating weight of 50 mg $dm^2$ and gelatin coating weight of 97 mg $dm^2$.

All the emulsions were then coated on subbed polyester at a silver coating weight of 50 mg $dm^2$ and a gelatin coating weight of 97 mg $dm^2$. After the coating had dried they were cut into strips exposed to light (1/50, 250 lux) and development in developer I (8 min).

Table 2 shows the foot speed measured when B, C, D and E were present in the emulsion at a range of compound concentrations.

TABLE 2

| Concentration | $S_{0.1}$ | | | |
|---|---|---|---|---|
| (mg per mol Ag) | Cpd B | Cpd C | Cpd D | Cpd E |
| 0 | 4.37 | 4.43 | 4.43 | 4.43 |
| 133 | 4.55 | 4.44 | 4.48 | 4.48 |
| 267 | 4.58 | 4.49 | 4.51 | 4.48 |
| 400 | 4.61 | 4.52 | 4.62 | 4.52 |

The results demonstrate that between 0.1-0.2 log E speed increases over an optimally chemically sensitised emulsion on addition of compounds of formula I were obtained.

TEST 3

Emulsion Optimally Chemically Sensitised and Panchromatically Sensitised

To the chemically sensitised emulsion as just prepared there was added a fixed amount (200 mg per mole of silver) of compound B and varying amounts of the panchromatic sensitising dye W of the formula Dye W $$\underset{(CH_2)_3SO_3^-}{\text{benzothiazole}}-CH=\underset{CH_3}{\overset{|}{C}}-CH=\underset{C_2H_5}{\text{benzothiazole}}$$

To another set of emulsions there was added the same amounts of dye W in the absence of Compound B.

All the emulsions were then coated on subbed polyester base at a silver coating weight of 50 mg dm$^2$ and a gelatin coating weight of 97 mg dm$^2$. After drying the strips were prepared from the coated material. One set of strips were then subjected to an overall 250 lux, white light exposure for 1/50 second then developed for eight minutes at 20° C. in the developer I. A second set of strips were then subjected to blue, green and red exposures (1/30s, 250 lux) respectively and were developed in developer II (10 min) of formula:

Developer II has the formula

| metol | 2 g |
|---|---|
| hydroquinone | 8 g |
| sodium sulphite | 90 g |
| sodium carbonate | 45 g |
| potassium bromide | 5 g |
| water to | 1 liter |

The results are shown in tables 3 and 4.

TABLE 3

| | $S_{0.1}$ | |
|---|---|---|
| [Dye W] (mg per mol of Ag) | With Cpd B | Without Cpd B |
| 0 | 4.56 | 4.54 |
| 67 | 4.90 | 4.71 |
| 133 | 5.14 | 4.86 |
| 200 | 5.14 | 4.91 |
| 267 | 5.16 | 4.92 |
| 383 | 5.11 | 5.00 |

These tables shows that the presence of Compound B increases the sensitivity of the emulsion over and above the sensitivity due to dye W alone.

TABLE 4

| [Dye W] (mg per mole of Ag) | Blue Speed ($S_{0.1}$) | | Green Speed ($S_{0.1}$) | | Red Speed ($S_{0.1}$) | |
|---|---|---|---|---|---|---|
| | With Cpd B | without Cpd B | With Cpd B | without Cpd B | With Cpd B | without Cpd B |
| 133 | 4.13 | 4.08 | 4.45 | 4.21 | 4.47 | 4.21 |
| 267 | 4.18 | 4.13 | 4.59 | 4.38 | 4.58 | 4.40 |

EXAMPLE 15

Using a Cubic Habit Silver Halide Emulsion

A polydisperse silver iodobromide emulsion containing 2.6 mol % iodide and having a median grain size of 0.48 μm was prepared. After the emulsion had been optimally chemically sensitised using sulphur and gold, then 350 mg of Compound B in methanol was added per mol of Ag on the emulsion. The emulsion was then stabilised using a tetraazaindolizine stabilizer and then coated on subbed polyester base at a coating weight of 1.54 g silver m$^2$ and gelatin coating weight of 1.38 g/m$^2$.

For comparison a similar emulsion was prepared and coated but without adding compound B. After exposure to blue light (200 Lux, 1 second) the following sensitometric parameters were measured after development in developer III for eight minutes at 20° C.

The formula of developer III is as follows:

| 1 Phenyl-3-pyrazolidinone | 1 g/l |
|---|---|
| Hydroquinone | 12.0 g/l |
| K$_2$SO$_3$ | 19.9 g/l |
| Na$_2$SO$_3$ | 38.0 g/l |
| Li$_2$SO$_3$ | 0.6 g/l |
| K$_2$CO$_3$ | 19.6 g/l |
| KHCO$_2$ | 13.3 g/l |
| KBr | 1.5 g/l |
| Benzotriazole | 0.5 g/l |
| Na$_4$EDTA 2 H$_2$0 | 4.0 g/l |
| KCH$_3$COO | 0.7 g/l |
| Ethylidiglycol | 50.0 g/l |
| water to 1 litre | |

The results are shown in Table 5.

TABLE 5

| COATING | MAX DENSITY | E 1 | E 2 | MIN DENSITY |
|---|---|---|---|---|
| Without Cpd B | 1.06 | 5.97 | 5.17 | 0.04 |
| With Cpd B | 1.23 | 6.27 | 5.49 | 0.05 |

E 1 = 6 - log exposure necessary to attain a density of 5% between D max. and D min.
E 2 = 6 - log exposure necessary to attain an optimal density of 50% between D max. and D min.

This shows that compound B of formula I increases the sensitivity of the emulsion over and above the natural sensitivity of the emulsion to blue light.

EXAMPLE 16

Using a Cubic Habit Silver Halide Emulsion

A polydisperse silver iodobromide emulsion containing 5.2 Mol % iodide and having a median grain size of 0.36 μm was prepared. After the emulsion had been optimally chemically sensitised using sulphur and gold 132 g per mole of Ag of the stabilizer of the formula

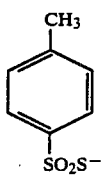

was added with stirring for 2 minutes. Then 640 mg per mole of Ag of Compound B and 289 mg of the green sensitising dye Y per mole of silver were added to the emulsion as a methanolic solution.

The formula of dye Y is

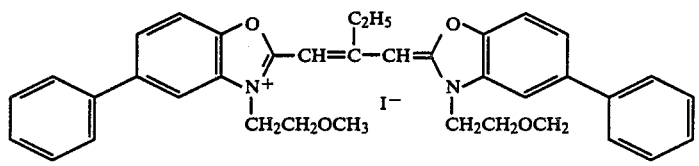

The emulsion was then coated on subbed polyester base at a silver coating weight of 1.41 g/m² and a gelatin coating weight of 1.75 g/m².

A similar coating was prepared which contained the above amount of dye Y but no Compound B.

Both coatings were then subjected to 200 lux exposure to green light for three different exposure times (t). The coatings were then developed in developer III for 8 minutes at 20° C.

The following results were obtained.

TABLE 6

| Coating | Max. density | Min. density | E 2 t = 1 s | E 2 512 s | E 2 1024 s |
|---|---|---|---|---|---|
| With cpd B and dye Y | 1.31 | 0.10 | 5.81 | 5.18 | 5.13 |
| With only dye Y | 1.33 | 0.08 | 5.81 | 5.04 | 4.96 |

This shows that the presence of compound B increases green speed at long exposure times (t) by decreasing low intensity reciprocity failure.

We claim:

1. A photographic silver halide negative working emulsion which comprises a monomethine compound of the general Formula I:

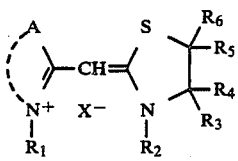

where A represents the atoms necessary to complete a benzoxazole or naphthoxazole ring which is optionally substituted, $R_1$ and $R_2$ are each alkyl, hydroxyalkyl or alkoxy alkyl groups wherein the alkyl moiety comprises 1 to 4 carbon atoms, $R_3$, $R_4$, $R_5$ and $R_6$ are each hydrogen atoms or alkyl groups having 1 to 4 carbon atoms or phenyl groups, and X is an anion.

2. A photographic silver halide negative working emulsion of claim 1 wherein in the monomethine compound of Formula I A represents the atoms necessary to complete a benzoxazole or naphthazole ring which is unsubstituted or is substituted by alkyl or alkoxy each having 1 to 4 carbon atoms, halogen or phenyl, $R_1$ and $R_2$ are each alkyl or alkoxy alkyl wherein the alkyl moiety comprises 1 to 4 carbon atoms, $R_3$, $R_4$, $R_5$ and $R_6$ are each hydrogen, alkyl having 1 to 4 carbon atoms or phenyl and $X^-$ is $ClO_4^-$, $BF_4^-$, or a halide.

3. A photographic silver halide negative working emulsion according to claim 2 wherein in the monomethine compound, both $R_1$ and $R_2$ are methyl groups.

4. A photographic silver halide negative working emulsion according to claim 1 wherein the monomethine compound is a compound of one of the following formulas:

Compound A

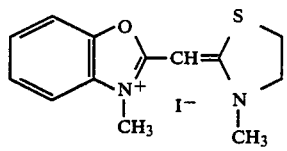

Compound B

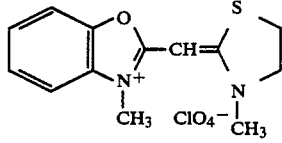

Compound C

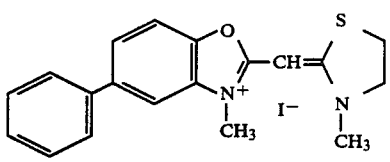

Compound D

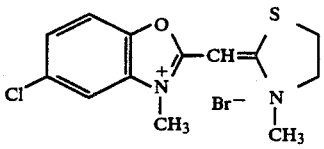

Compound E

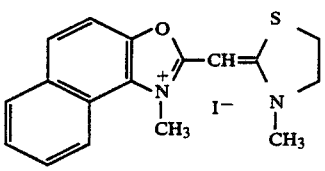

Compound F

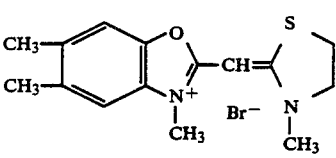

-continued

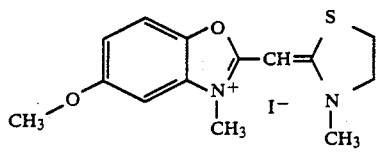
Compound G

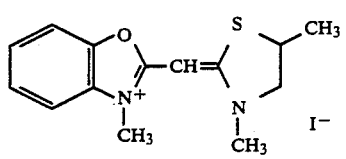
Compound H

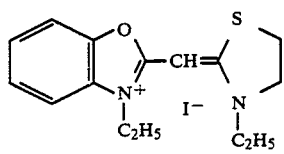
Compound I

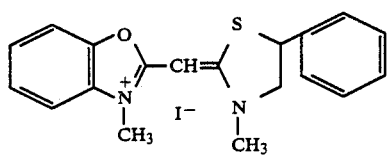
Compound J

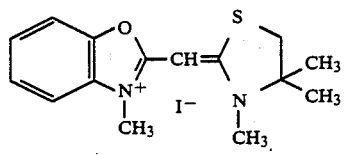
Compound K

-continued

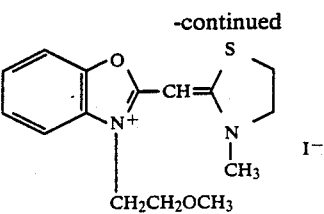
Compound L

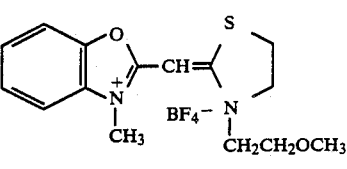
Compound M

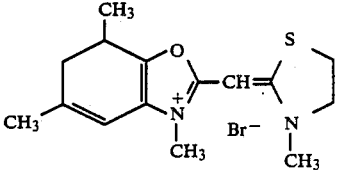
Compound N

5. A photographic silver halide negative working emulsion according to claim 1 wherein the amount of monomethine compound of Formula I is from 50 mg per mole of silver to 700 mg per mole of silver.

6. A photographic silver halide negative working emulsion according to claim 1 wherein the silver halide grains present are of the tabular habit having an aspect ratio of greater than 5:1.

7. A photographic silver halide negative working emulsion according to claim 6 wherein the amount of monomethine compound of Formula I is from 100 mg per mole of silver to 400 mg per mole of silver.

8. A photographic silver halide negative working emulsion according to claim 1 wherein the silver halide grains present are polydisperse having a cubic habit.

9. A photographic silver halide negative working emulsion according to claim 8 wherein the amount of monomethine compound of Formula I is from 350 mg per mole of silver to 650 mg per mole of silver.

10. A photographic silver halide material which comprises a support and at least one silver halide negative working emulsion layer as claimed in claim 1.

* * * * *